(12) United States Patent
Tanaka et al.

(10) Patent No.: US 7,253,333 B2
(45) Date of Patent: Aug. 7, 2007

(54) DROSOPHILA STRAIN CARRYING BRADEION GENE(S) TRANSFERRED THEREINTO

(75) Inventors: Manami Tanaka, Ibaraki (JP); Masamitsu Yamaguchi, Kyoto (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/469,356

(22) PCT Filed: Feb. 26, 2002

(86) PCT No.: PCT/JP02/01755

§ 371 (c)(1), (2), (4) Date: Feb. 3, 2004

(87) PCT Pub. No.: WO02/067670

PCT Pub. Date: Sep. 6, 2002

(65) Prior Publication Data

US 2004/0117864 A1    Jun. 17, 2004

(30) Foreign Application Priority Data

Feb. 28, 2001    (JP)    ............... 2001-054759

(51) Int. Cl.
*A01K 67/00*    (2006.01)
*A01K 67/033*    (2006.01)

(52) U.S. Cl. ................. 800/8; 800/9; 800/10

(58) Field of Classification Search ............ 800/13; 435/320.1, 455, 325
See application file for complete search history.

(56) References Cited

FOREIGN PATENT DOCUMENTS

JP    2000-139470    5/2000

OTHER PUBLICATIONS

Kramer et al. (2003) GAL4 causes developmental defects and apoptosis when expressed in the developing eye of Drosophila melanogaster Genetics and Molecular Research, 2:43-47.*

Tanka et al. (2001) Characterization of Tissue- and Cell-Type-Specific Expression of a Novel Human Septin Family Gene, Bradeion; Biochemical and Biophysical Communications. 286: 547-553.* http://flystocks.bio.indiana.edu/Fly_Work/culturing.htm (2006) pp. 1-5.*

Jackson, "Polyglutamine-Expanded Human Huntingtin Transgenes Induce Degeneration of Drosophila Photoreceptor Neurons", Neuron, vol. 21, 633-642, Sep. 1998.

Brand et al. "Targeted gene expression as a means of altering cell fates and generating dominant phenotypes", Development 188, 401-415 (1993).

Yamaguchi et al., "Ectopic expression of human p53 inhibits entry into S phase and induces apoptosis in the Drosophila eye imaginal disc," *Oncogene*, 1999, pp. 6767-6775, vol. 18, Stockton Press, UK.

Hirose et al., "Ectopic expression of DREF Induces DNA Synthesis, Apoptosis, and Unusual Morphogenesis in the Drosophila Eye Imaginal Disc: Possible Intereaction with Polycomb and trithorax Group Proteins," *Molecular and Cellular Biology*, Nov. 2001, pp. 7231-7242, vol. 21, American Society for Microbiology.

* cited by examiner

*Primary Examiner*—Valarie Bertoglio
(74) *Attorney, Agent, or Firm*—Foley & Lardner LLP

(57) ABSTRACT

Provided is a special *Drosophila* strain having a Bradeion gene artificially incorporated therein to exclusively express the gene in the compound eyes and thus to exhibit rough eye. The *Drosophila* strain has the following properties:
(a) a human-derived Bradeion gene has been transferred in the strain to express the human-derived protein Bradeion in the compound eyes from the developmental period;
(b) the compound eyes show morphological abnormality due to the expression of Bradeion; and
(c) the morphological abnormality occurring in the compound eyes is multiplied according to the number of transferred Bradeion genes.

1 Claim, 3 Drawing Sheets

FIG. 2A GMR-GAL4; +
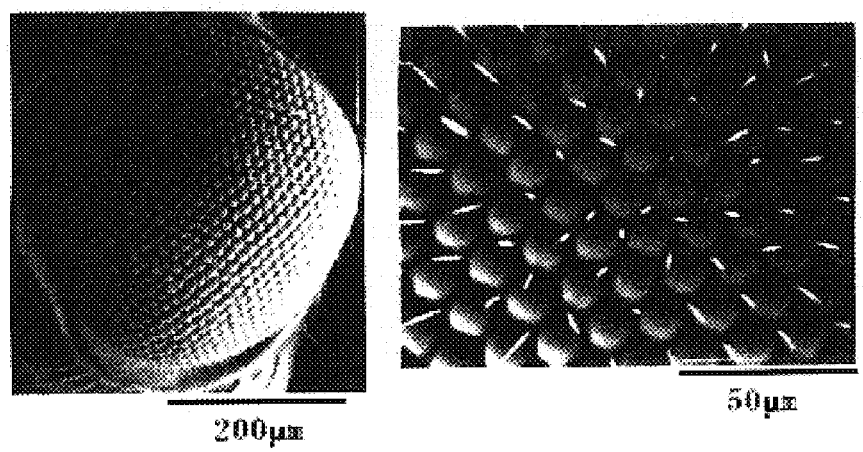
FIG. 2B GMR-GAL4; UAS-Bradeionβ/ +
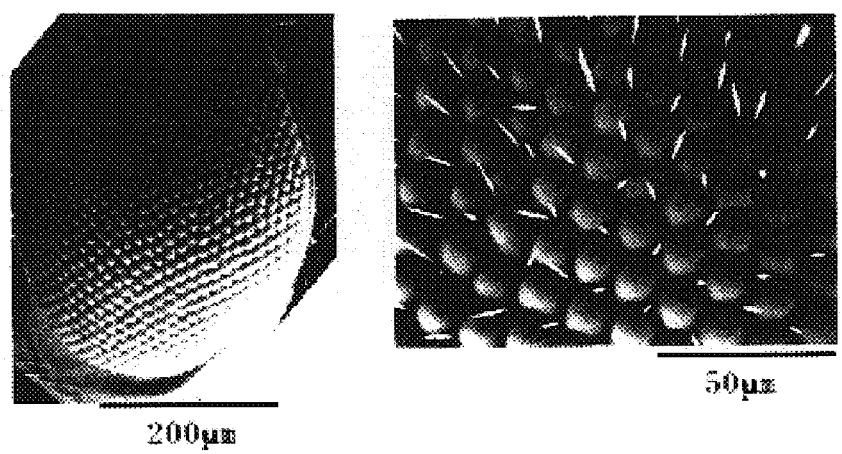
FIG. 2C GMR-GAL4; UAS-Bradeionβ/ UAS-Bradeionβ
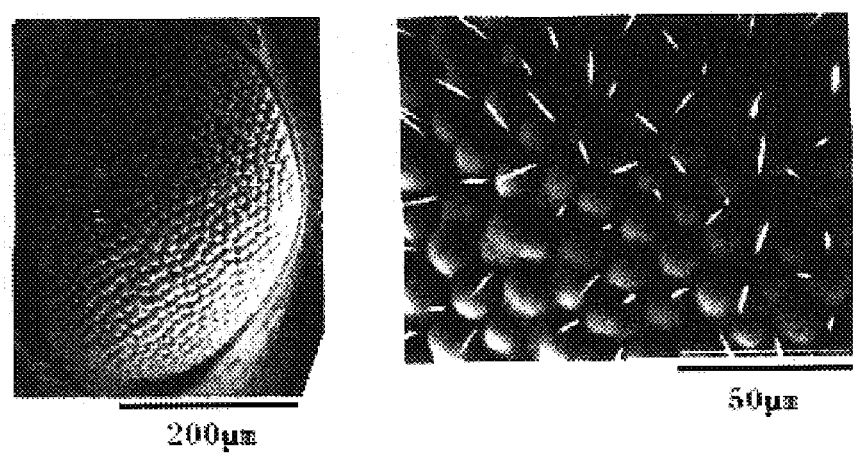

FIG. 3A  GMR-GAL4; UAS-Bradeion β
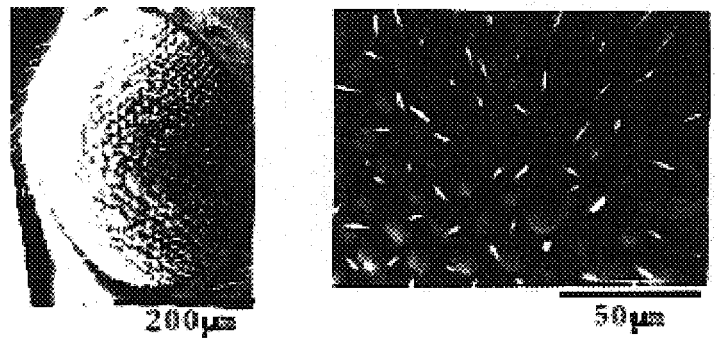
FIG. 3B  GMR-GAL4; UAS-Bradeion β; GMR-DIAP1
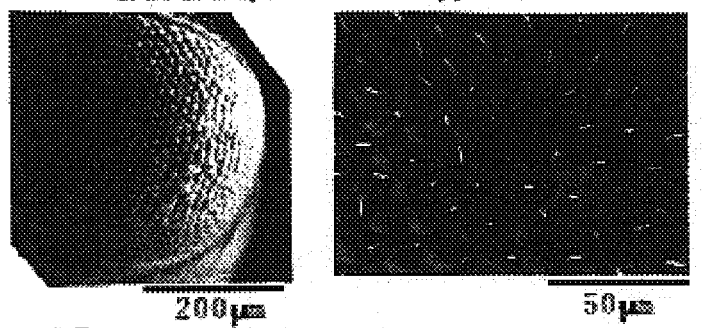
FIG. 3C  GMR-GAL4; UAS-Bradeion β; GMR-DIAP2
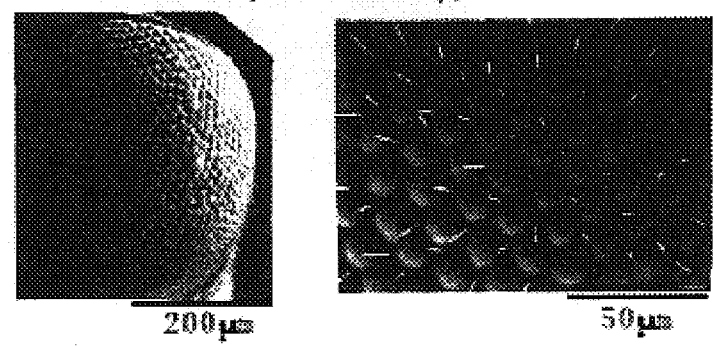
FIG. 3D  GMR-GAL4; UAS-Bradeion β; GMR-P35
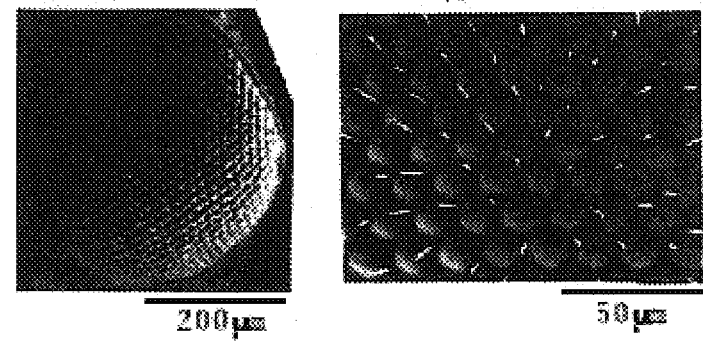

SEQUENCE LISTING

<160> NUMBER OF SEQ ID NOS: 2

<210> SEQ ID NO 1
<211> LENGTH: 2274
<212> TYPE: DNA
<213> ORGANISM: Homo sapiens
<220> FEATURE:
<221> NAME/KEY: mat_peptide
<222> LOCATION: (129)...(1943)

<400> SEQUENCE: 1

| | | | | | |
|---|---|---|---|---|---|
| gaaaggagca | agccaggaag | ccagacaaca | acagcatcaa | acaaggctg | tttctgtgtg | 60 |
| tgaggaactt | tgcctgggag | ataaaattag | acctagagct | ttctgacagg | gagtctgaag | 120 |
| cgtgggacat | ggaccgttca | ctgggatggc | aagggaattc | tgtccctgag | gacaggactg | 180 |
| aacctgggat | caaccgtttc | ctggaggaca | ccacggatga | tggagaactg | agcaagttcg | 240 |
| tgaaggattt | ctcaggaaat | gcgagctgcc | acccaccaga | ggctaagacc | tgggcatcca | 300 |
| ggccccaagt | cccggagcca | aggcccccagg | ccccggacct | ctatgatgat | gacctggagt | 360 |
| tcagaccccc | ctcgcggccc | cagtcctctg | acaaccagca | gtacttctgt | gccccagccc | 420 |
| ctctcagccc | atctgccagg | ccccgcagcc | catgggggga | gcttgatccc | tatgattcct | 480 |
| ctgaggtaga | gcctccagcc | ctgcctttgc | ctttcagtgg | gctgctgcag | gaagaccggg | 540 |
| ggcagggagc | aggaatgtgt | gtgtgtgtgt | gtgtgtgtgt | gtgtgtgtgt | gtgtttgtgt | 600 |
| gtgtgtgtat | ctgggaccca | tttcagtcct | gtgtcagccc | tagctccaaa | atatctgccc | 660 |
| ccaagggcac | tggaaatttg | cagtttcagc | aagggcagga | ggcccagctg | gtggcctcag | 720 |
| atgggaactc | acagaagtct | ggcactgctt | ttttaaggct | ggggcaaagg | cctgaaaggg | 780 |
| agagaagatt | ggcgctgggt | gccggggccc | ctttggctcc | tcaccgtgat | gcattctgcc | 840 |
| ttcctgtcta | ctacgatgac | aaggagtatg | tgggcttt gc | aaccctcccc | aaccaagtcc | 900 |
| accgaaagtc | cgtgaagaaa | ggctttgact | ttaccctcat | ggtggcagga | gagtctggcc | 960 |
| tgggcaaatc | cacacttgtc | aatagcctct | tcctcactga | tctgtaccgg | gaccggaaac | 1020 |
| ttcttggtgc | tgaagaaagg | atcatgcaaa | ctgtggagat | cactaagcat | gcagtggaca | 1080 |
| tagaaaaaaa | aggtgtgagg | ctgcggctca | ccattgtgga | cacaccaagt | tttggggatg | 1140 |
| cagtcaacaa | cacagagtgt | atgtctgact | ggaagcctgt | ggcagaatac | attgatcagc | 1200 |
| agttt gagca | gtatttccga | gacgagagtg | gcctgaaccg | aaagaacatc | caagacaaca | 1260 |
| gggtgcactg | ctgcctgtac | ttcatctcac | ccttcggcca | tgggctccgg | ccattggatg | 1320 |
| ttgaattcat | gaaggccctg | catcagcggg | tcaacatcgt | gcctatcctg | gctaaggcag | 1380 |
| acacactgac | acctcccgaa | gtggaccaca | agaaacgcaa | aatccgggag | gagattgagc | 1440 |
| attttggaat | caagatctat | caattcccag | actgtgactc | tgatgaggat | gaggacttca | 1500 |
| aattgcagga | ccaagcccta | aaggaaagca | tcccatttgc | agtaattggc | agcaacactg | 1560 |
| tagtagaggc | cagagggcgg | cgagttcggg | gtcgactcta | ccctgggc | atcgtggaag | 1620 |
| tggaaaaccc | agggcactgc | gactttgtga | agctgaggac | aatgctggta | cgtacccaca | 1680 |
| tgcaggacct | gaaggatgtg | acacgggaga | cacattatga | aactaccgg | gcacagtgca | 1740 |
| tccagagcat | gacccgcctg | gtggtgaatg | aacggaatcg | caagtatgac | cagaagccag | 1800 |
| gacaaagctg | gcaggggggag | atcccaagcc | tagccttggg | tgagaccaag | ccctactttt | 1860 |
| gttcttctat | aggccctggg | ctcaatctaa | gcgggtgctg | gggtcctcct | cgccttatca | 1920 |

-continued

| | | | | |
|---|---|---|---|---|
| accctttttct | ccctttagca | aactgactcg | ggaaagtggt | accgacttcc ccatccctgc | 1980 |
| tgtcccacca | gggacagatc | cagaaactga | gaagcttatc | ccagagaaag attaggagct | 2040 |
| gcggcggata | cacgagatac | tacaccaaat | accaaaacag | ataaaggaga actatttact | 2100 |
| ggctttcagc | cctggatatt | taaatctcct | cctcttcttc | ctgtccatgc cggcccctcc | 2160 |
| cagcaccagc | tctgctcagg | cccctttcagc | tactgccact | tcgccttaca tccctgctga | 2220 |
| ctgcccagag | actcagagga | aataaagttt | aataaatctg | taggtggctt ctgg | 2274 |

<210> SEQ ID NO 2
<211> LENGTH: 1735
<212> TYPE: DNA
<213> ORGANISM: Homo sapiens
<220> FEATURE:
<221> NAME/KEY: mat_peptide
<222> LOCATION: (129)...(1562)

<400> SEQUENCE: 2

| | | | | |
|---|---|---|---|---|
| gaaaggagca | agccaggaag | ccagacaaca | acagcatcaa | acaaggctg tttctgtgtg | 60 |
| tgaggaactt | tgcctgggag | ataaaattag | acctagagct | ttctgacagg gagtctgaag | 120 |
| cgtgggacat | ggaccgttca | ctgggatggc | aagggaattc | tgtccctgag acaggactg | 180 |
| aagctgggat | caagcgtttc | ctggaggaca | ccacggatga | tggagaactg agcaagttcg | 240 |
| tgaaggattt | ctcaggaaat | gcgagctgcc | acccaccaga | ggctaagacc tgggcatcca | 300 |
| ggccccaagt | cccggagcca | aggccccagg | ccccggacct | ctatgatgat gacctggagt | 360 |
| tcagaccccc | ctcgcggccc | cagtcctctg | caaccagca | gtacttctgt gccccagccc | 420 |
| ctctcagccc | atctgccagg | ccccgcagcc | catggggcaa | gcttgatccc tatgattcct | 480 |
| ctgaggatga | caaggagtat | gtgggctttg | caaccctccc | caaccaagtc caccgaaagt | 540 |
| ccgtgaagaa | aggctttgac | tttacccctca | tggtggcagg | agagtctggc ctgggcaaat | 600 |
| ccacacttgt | caatagcctc | ttcctcactg | atctgtaccg | ggaccggaaa cttcttggtg | 660 |
| ctgaagagag | gatcatgcaa | actgtggaga | tcactaagca | tgcagtggac atagaagaga | 720 |
| agggtgtgag | gctgcggctc | accattgtgg | acacaccagg | ttttggggat gcagtcaaca | 780 |
| acacagagtg | ctggaagcct | gtggcagaat | acattgatca | gcagtttgag cagtatttcc | 840 |
| gagacgagag | tggcctgaac | cgaaagaaca | tccaagacaa | cagggtgcac tgctgcctgt | 900 |
| acttcatctc | acccttcggc | catgggctcc | ggccattgga | tgttgaattc atgaaggccc | 960 |
| tgcatcagcg | ggtcaacatc | gtgcctatcc | tggctaaggc | agacacactg acacctcccg | 1020 |
| aagtggacca | caagaaacgc | aaaatccggg | aggagattga | gcattttgga atcaagatct | 1080 |
| atcaattccc | agactgtgac | tctgatgagg | atgaggactt | caaattgcag gaccaagccc | 1140 |
| taaaggaaag | catcccattt | gcagtaattg | gcagcaacac | tgtagtagag gccagagggc | 1200 |
| ggcgagttcg | gggtcgactc | tacccctggg | gcatcgtgga | agtggaaaac ccagggcact | 1260 |
| gcgactttgt | gaagctgagg | acaatgctgg | tacgtaccca | catgcaggac ctgaaggatg | 1320 |
| tgacacggga | gacacattat | gagaactacc | gggcacagtg | catccagagc atgacccgcc | 1380 |
| tggtggtgaa | ggaacggaat | cgcaacaaac | tgactcggga | aagtggtacc gacttcccca | 1440 |
| tccctgctgt | cccaccaggg | acagatccag | aaactgagaa | gcttatccga gagaaagatg | 1500 |
| aggagctgcg | gcggatgcag | gagatgctac | acaaaataca | aaaacagatg aaggagaact | 1560 |
| attaactggc | tttcagccct | ggatatttaa | atctcctcct | cttcttcctg tccatgccgg | 1620 |

| | |
|---|---|
| ccctcccag caccagctct gctcaggccc cttcagctac tgccacttcg cctaacatcc | 1680 |
| ctgctgactg cccagagact cagaggaaat aaagtttaat aaatctgtag gtggc | 1735 |

DROSOPHILA STRAIN CARRYING BRADEION GENE(S) TRANSFERRED THEREINTO

TECHNICAL FIELD

The present invention relates to a special *Drosophila* strain and the use thereof. Specifically, the special *Drosophila* strain is generated by artificially incorporating a Bradeion gene, which encodes a protein involved in the long-term survival and the maintenance of the neurotransmission of human cranial nerve cells, into *Drosophila melanogaster*, which is an experimental insect and is essential for genetic and molecular biological analyses, to exclusively express the gene in the insect's compound eyes and thus to develop rough eye.

BACKGROUND ART

The molecular medicine revolution of the 21st century aims at, as a post-genome project, the construction of a control monitor system suited for individual characteristics by capturing genes and substances that form the basis of disease. Specifically, the system is intended to establish a medical system that is specific to individual gene types through the detection (via diagnosis and gene monitoring) of risk groups from disease groups that are thought to threaten daily social activities based on the concept of "Quality of Life" and include genetic diseases, cancer and neurodegenerative diseases, the finding of the risk genes of these disease groups, and the searching for the sensitivity against therapy (drug and gene therapy). Here, not only cancer, but also many diseases are multi-gene effects and largely depend on environmental factors. Thus, it is impossible to prevent a disease by controlling a single factor. However, it is possible to take measures to control disease through the development of so-called control technology that controls the conditions of an individual with a disease.

Now based on this concept, in particular control technology to counter the canceration and the immortalization of cells is actively developed at the molecular level. Specifically, in the studies of technology to control cellular life span, signal transduction is often analyzed. Through these studies, various molecular bases involved in cell proliferation, division and canceration have been revealed. The secretary of the Agency of Industrial Science and Technology has already applied for a patent for Bradeion, which is such a factor controlling cellular life span (JP Patent Publication (Kokai) No. 2000-139470, JP Patent Application No. 2000-308650 and U.S. patent application Ser. No. 09/440,936). This patent application has revealed that Bradeion, which is expressed in cancer and particularly expressed only in colon cancer cells or skin cancer, is naturally useful in early diagnosis, and also satisfies various conditions required of a specific inhibitor or a gene therapy target.

If such a signaling substance is found, only analytical results at the culture cell level can be obtained with conventional techniques. To further develop disease control or gene function control technology, which is an original purpose, the presence of an appropriate organism model is required. Currently, a special genetically-modified animal such as a knockout mouse is used for this purpose.

DISCLOSURE OF THE INVENTION

However, the generation of knockout mice and transgenic mice involves considerable difficulties. In addition, gene expression is knocked out from the developmental period, so that, for example, the applicable range and successful examples of such mice are limited. Thus, they cannot be said to be organism models that can satisfy broad demands.

In recent years, the usability of a fruit fly, *Drosophila melanogaster*, has been much publicized in comparison with that of mammalian models such as mice. Originally, the use of *Drosophila* was established as an experimental system for transformation by genetic breeding in the field of genetics in a manner similar to those for corn and peas. Recently, it has begun to be shown that a mutation in an individual trait of *Drosophila* can reflect a human trait better than a mammalian model, depending on the characteristics of the relevant gene group. In particular, *Drosophila* is highly useful for gene groups involved in the above-described signal transduction, signal transduction system and cellular life span.

The experimental system using *Drosophila* involves transferring a human gene involved in the above signal transduction system into the compound eye formation system. Specifically, it limits the expression vector, so that the gene is expressed exclusively in the compound eye formation system (pUAST and the like, see FIGS. 1 to 3). The compound eye formation system of insects normally comprises a large number of the cells involved in the formation, as previously known. During the developmental period, the consistency system acts to fix the cell cycle at G0/G1, so that the same cell cycle is maintained. After the fixation, the cells differentiate into so-called optic nerve cells. That is, this system can also be used for a system for testing a gene function (nerve cell differentiation potency). Reasons why biofunction tests for genes using *Drosophila* are now being used so generally are conditions: 1) the system is useful for signal transduction genes; 2) the system can test neuronal differentiation potency; 3) the system uses a human gene, so as to be able to reflect a human function better than that reflected by a mouse; and 4) a mutation due to gene transfer is expressed exclusively in the compound eyes, so as to be able to avoid the disintegration of the experimental system due to death during development, unlike the case of knockout mice. Added herein is its usability as a gene breeding system. All the genes and substance groups do not function individually, but are present as substance groups or the functional protein assemblies that are involved in a certain function within a cell or an organism. Therefore, the precise capturing of functional dynamics of the whole pathway, in which the groups or the assemblies are involved, directly relates to the understanding of abnormalities in an organism, such as a disease. *Drosophila* flies can be genetically crossed with each other. Crossing with a group having a transgene or with a *Drosophila* group having a known genetic mutation can reveal a gene group involved in the transgene through the observation of individual mutations under physiological conditions.

Yamaguchi (one of the inventors) et al. have previously published a paper wherein it is shown that the gene transfer of a human cellular life span and cell death-determining factor p53 into the compound eye formation system of *Drosophila* enables the good reproduction of the cell death-inducing function at an individual level. Specifically, the process begins from the detection of the abnormal pathway of cells and tissue that have become cancerous, and the detection of causative genes involved in the pathway and the mutations. At the next step, the elucidation of substance groups to which these detection results are linked and the elucidation of the functions of the substance groups as an assembly are enabled in an individual model under physiological conditions. Only with such a series of analyses, disease control can be achieved.

The Bradeion gene-transferred *Drosophila* strain, with which the cancer-specific correlation of a conventionally known gene and substance groups can be elucidated. This is carried out through a series of analyses concerning the elucidation of the signal transduction mechanism involved in cancer cell proliferation and division mediated by Bradeion, the detection of signaling substance groups within a cancer cell, and the elucidation of the dynamics thereof. Although Bradeion originally regulates the entry into the M-phase of the cell cycle during cell proliferation and division, it is observed in a human to show strong cell-specific expression and have a cell cycle-regulating function in colon cancer cells. Thus, it is assumed to be a key substance that enables the analysis of the abnormal homeostasis of cell groups that have been transformed to develop cancer. Furthermore, it is considered that Bradeion evidently functions by binding and associating with various substances participating in intracytoplasmic signal transduction.

The present invention can provide a new development of cancer control technology through analyses concerning the artificial re-transformation of cells and cell death induction by elucidating the signal transduction system that maintains cell division and proliferation within cancer cells, and provides the underlying data thereof.

Specifically, the results of these studies finally contribute to precise and cost-effective diagnosis, treatment and prophylaxis suited for individual gene type through cancer cell gene monitoring (diagnosis of cancer) and cancer cell division and proliferation control (gene therapy).

That is, the present invention is as described below.
(1) A *Drosophila melanogaster* strain, having the following properties:
(a) a human-derived Bradeion gene has been transferred in the strain to express the human-derived protein Bradeion in the compound eyes from the developmental period;
(b) the compound eyes show morphological abnormality due to the expression of Bradeion; and
(c) the morphological abnormality occurring in the compound eyes is multiplied according to the number of transferred Bradeion genes.
(2) The *Drosophila melanogaster* strain of (1), wherein the morphological abnormality in the compound eyes is referred to as "rough eye," in which the cell cycles of each single eye are inconsistent.
(3)
(d) The *Drosophila melanogaster* strain of (1) or (2), which can be genetically crossed with other strains of *Drosophila*, which is able to transmit a trait introduced by the transferred Bradeion gene to the offspring, and which is able to inherit the inherited traits of other *Drosophila* strains to be crossed therewith.

The Bradeion gene can be obtained by purifying mRNA from human brain tissue, constructing a cDNA library and selecting the positive clone. A human Bradeion gene to be transferred into *Drosophila* includes DNA that can hybridize under stringent conditions to Bradeion DNA. Here, the term "stringent conditions" refers to conditions wherein hybridization occurs only when 90% or more, preferably 95% or more, and more preferably 97% or more homology is present between the Bradeion DNA sequence and the other sequence. Normally, under such conditions, hybridization occurs at approximately 5° C. to approximately 30° C., and preferably at approximately 10° C. to approximately 25° C., below the melting temperature of the complete hybrid. The stringent conditions are described in J. Sambrook et al., Molecular Cloning, A Laboratory Mannual, Second Edition, Cold Spring Harbor Laboratory Press (1989), and the conditions described therein can be employed. DNA capable of hybridizing under stringent conditions to the Bradeion DNA encodes a Bradeion analogue. Here, the analogue has characteristics substantially equivalent to those of human-derived Bradeion, and has an amino acid sequence derived from the amino acid sequence of human Bradeion by deletion, substitution or addition of at least one amino acid. The analogue preferably has 90% or more, preferably 95% or more, and more preferably 97% or more homology with Bradeion. Bradeion includes both a human a Bradeion and a human β Bradeion. The Bradeion gene can be obtained by a method disclosed in JP Patent Publication (Kokai) No. 2000-139470. In addition, DNA containing α Bradeion cDNA was deposited with the International Patent Organism Depositary, National Institute of Advanced Industrial Science and Technology (Chuo-6, 1-1-1, Higashi, Tsukuba-shi, Ibaraki, Japan) on Jul. 14, 1998, under FERM BP-6922. Furthermore, the α Bradeion gene and the β Bradeion gene were respectively deposited under accession Nos. E37353 and AB008753 or E37354 with the Gene Bank.

Moreover, the sequence of the a Bradeion gene is represented by SEQ ID NO: 1, and the sequence of the β Bradeion gene is represented by SEQ ID NO: 2. The entire sequence of SEQ ID NO: 1 or 2 may be transferred into *Drosophila*, or a portion ranging from positions 129 to 1943 of SEQ ID NO: 1 encoding a mature peptide (mat_peptide) of the α Bradeion protein, and a portion ranging from positions 129 to 1562 of SEQ ID NO: 2 encoding a mature peptide of the β Bradeion protein may be transferred into *Drosophila*.

The Bradeion gene can be transformed into *Drosophila* using, for example, a pUAST vector (Brand, A. H. and Perrimon, N. (1993) Development, 118, 401-415). The transferred Bradeion gene can be expressed specifically in the compound eye primordium using a GAL4-UAS target expression system (Brand, A. H. and Perrimon, N. (1993) Development, 118, 401-415.), thereby causing a morphological abnormality in the imaginal compound eyes. A fly having the Glass-GAL4 gene (optic primordium-specific Gal4 expression) is crossed with a fly having the UAS-Bradeion gene. The resulting *Drosophila* expresses Bradeion specifically in the optic primordium by transactivation of Bradeion, as shown in FIG. 1. The morphological abnormality resulting from Bradeion expression is referred to as "rough eye," wherein the cell cycles of each single eye of the compound eyes are inconsistent. At this time, the morphological abnormality is enhanced by increasing the number of copies of the Bradeion gene to be transferred. Other biological characteristics of the *Drosophila* strain of the present invention are the same as those of normal *Drosophila* strains.

The *Drosophila* strain of the present invention can be crossed with other strains of *Drosophila*, can transmit the Bradeion gene transferred by crossing and genes of other strains used for crossing to the offspring, and can transmit a trait that is expressed by the transferred Bradeion gene and the inherited traits of other strains to the offspring.

The thus obtained *Drosophila* strain of the present invention can be stored and sent in the form of eggs.

A mutation that modifies the rough-eye phenotype resulting from the over-expression of Bradeion can be screened for by the following method. Specifically, approximately 200 *Drosophila* strains having deletion chromosomes (the sum of the chromosomal deletion regions of these strains corresponds to approximately 70% of the entire genome of *Drosophila*) are obtained from the Invertebrate Genetics Laboratory, Genetic Strain Research Center, National Institute of Genetics. Then, these strains are successively crossed with gene-transferred *Drosophila* strains showing a morphological abnormality in their compound eyes to transmit heterozygous deletion chromosomes to the offspring. Screening is then performed for strains wherein the morphological abnormality in the compound eyes is suppressed or enhanced. Then, lethal mutant strains (available from the genome projects in the U.S. and Europe) in which P-element has been inserted within the chromosomal region showing suppression or enhancement due to deletion (which is shown as a result of these crossing experiments) are collected, and then similar crossing experiments can be conducted.

Furthermore, a novel molecular target of a therapeutic agent for diagnosing cancer using Bradeion as an indicator can also be searched for by the following method. Specifically, the above lethal mutant strains into which P-element has been inserted showing the suppressed or enhanced phenotype are obtained, and then genes that are inactivated by P-element insertion are cloned by the P-element plasmid rescue method. The partial nucleotide sequences of the cloned genes are determined, the gene products thereof are identified by searching the database, and then human homologues thereof are cloned using a standard method. In addition, analysis is made for the genetic interaction between the thus obtained lethal mutant strains into which P-element has been inserted and the mutant strains of a known gene for regulating higher order chromosome structure, a cell cycle-related gene or an apoptosis-related gene.

Moreover, a candidate for a novel anticancer agent can be searched for by screening for an agent that suppresses the morphological abnormality exhibited by the thus established gene-transferred *Drosophila*.

The present invention will be described more specifically by the following examples. These examples are not intended to limit the present invention.

BRIEF DESCRIPTION OF THE DRAWINGS

The application contains at least one photograph executed in black and white. Copies of this patent or patent application publication with black and white photographs will be provided by the Office upon request and payment of the necessary fee.

FIG. 2 Shows that expression of Bradeion β in eye imaginal disc induces a rough eye phenotype. Scanning electron micrographs of adult compound eyes of a flies (A) a control, having a genotype of GMR-GAL4 and no Bradeion β gene, (B), having a genotype of GMR-GAL4 and one copy of the UAS-Bradeion β gene, (C) having a genotype GMR-GAL4 and two copies of the UAS-Bradeion β gene. Magnification: (right panels), 200×; and (left panels), 800×. As shown in FIGS. 2A to 2C, a fly (A) did not have a morphological abnormality. Flies (B) and (C) into which one or more Bradeion β genese were incorporated had a morphological abnormality.

FIG. 3 Shows that expression of apoptosis inhibitors suppressed the Bradeion β induced rough eye phenotype. Scanning electron micrographs of adult compound eyes of a fly (A), having a genotype of GMR-GAL4 and UAS Bradeion, (B), GMR-GAL4 and UAS-Bradeionβ/GMR-DIAP1, (C) GMR-GAL4 and UAS Bradeion β/GMR-DIAP2, (D), GMR-GAL4 and UAS-Bradeion β/GMR-P35. Magnification: (right panels), 200×; and (left panels), 800×. As shown in FIGS. 3A to 3D, a morphological abnormality was suppressed in a fly (B), fly (C) and fly (D) into which an anti-apoptosis gene was incorporated.

BEST MODE OF CARRYING OUT THE INVENTION

Example 1

Figure 1:
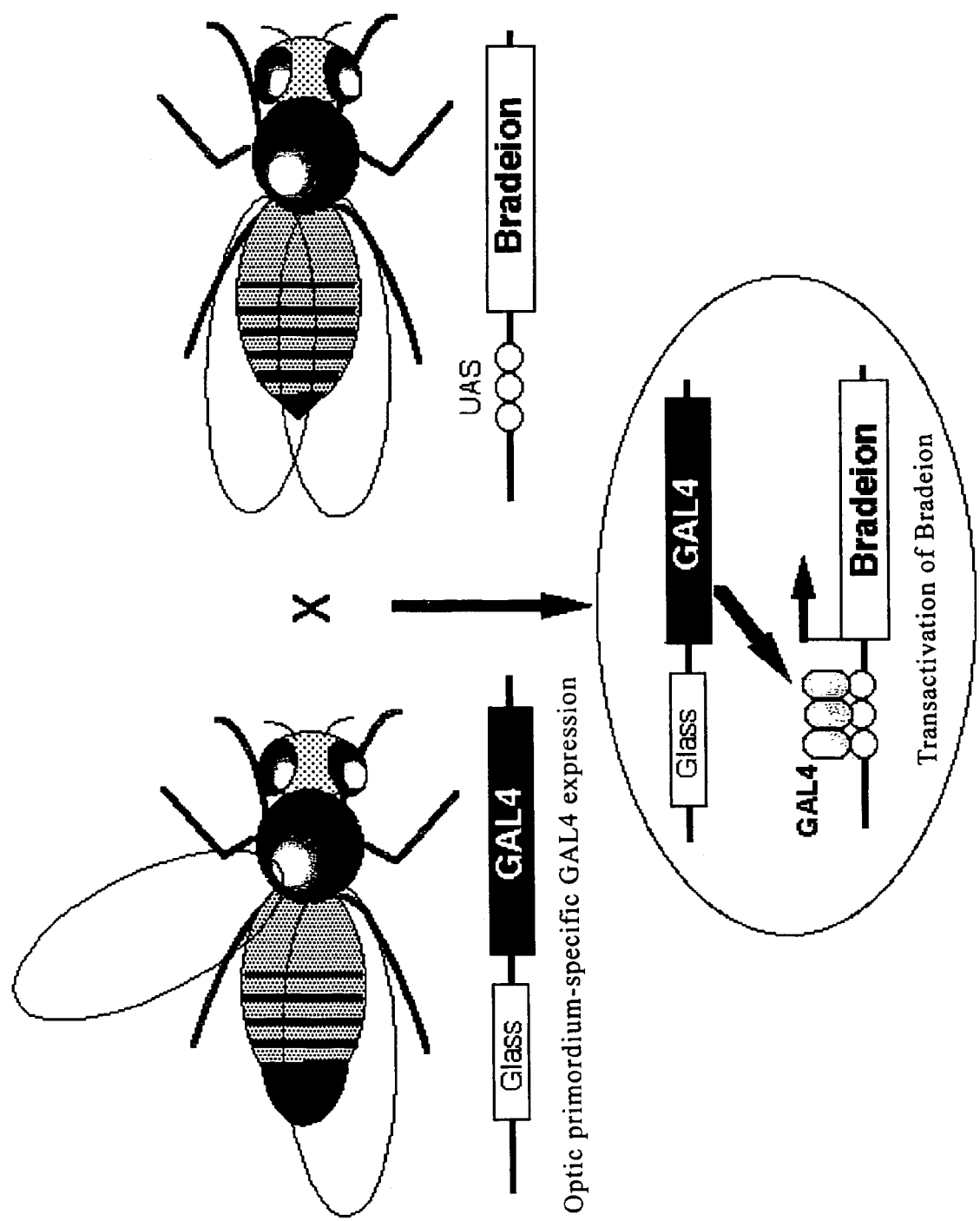
FIG. 1 is a schematic view showing a method for transferring the Bradeion gene into *Drosophila* so that gene can be expressed. In the method, a fly having the Glass-GAL4 gene is crossed with a fly having the UAS-Bradeion gene. In an offspring, Bradeion is expressed specifically in the optic primordium by transactivation of Bradeion by GAL4-UAS system.

Bradeion cDNA was ligated to Xho I-EcoR I (blunt-ended) cleavage site located downstream of a promoter having a transcription factor GAL4 binding sequence of a pUAST vector (Brand, A. H. and Perrimon, N. (1993). Development, 118, 401-415), thereby obtaining a recombinant plasmid DNA (pUAST-Bradeion). The DNA was transferred into *Escherichia coli* for transformation, and then the bacteria were grown (FIG. 1).

pUAST-Bradeion DNA was purified using a Qiagen column, and then injected in a minute amount into the fertilized eggs of a *Drosophila* strain, which is white gene (−) and has a transposase gene (Spradling, A. C. (1986). *Drosophila*: a practical approach. Roberts, D. B. (ed.). IRL Press: Oxford, pp. 175-197), and then a transformant that was rescued with a white gene marker present within the pUAST-Bradeion DNA was selected (Robertson, H. M., Preston, C. R., Philips, R. W., Johnson-Schlitz, D. M., Benz, W. K. and Engels, W. R. (1988). Genetics, 118, 461-470). The thus established strains are summarized in Table 1 below.

TABLE 1

| P-element plasmid | Strain | Chromosomal linkage |
|---|---|---|
| pUAS-Bradeion | 4 | II |
| | 19 | X |
| | 25 | III |
| | 27 | II |
| | 38 | II |
| | 46 | III |
| | 54 | II |

The compound eye primordium-specific over-expression of Bradeion using the GAL4-UAS target expression system (Brand, A. H. and Perrimon, N. (1993). Development, 118, 401-415) causes a morphological abnormality in the imaginal compound eyes (rough eye phenotype) (FIG. 2B) (FIG. 2A shows a control). The morphological abnormality was further enhanced by increasing the number of copies of a UAS-Bradeion gene (FIG. 2C). These morphological abnormalities were suppressed by the co-expression of *Drosophila* anti-apoptosis proteins DIAP1 (FIG. 3B) and DIAP2 (FIG. 3C), or Baculovirus anti-apoptosis protein P35 (FIG. 3D) in the compound eye primordium. Based on these results, it is considered that the over-expression of Bradeion induces apoptosis in the cells of the compound eye primordium, so as to cause a morphological abnormality in the imaginal compound eyes.

INDUSTRIAL APPLICABILITY

By the use of the Bradeion gene-transferred *Drosophila* strain of the present invention, precise and cost-effective diagnosis, treatment and prophylaxis suited for an individual gene type can be finally achieved through cancer cell gene monitoring (diagnosis of canceration) and the regulation of cancer cell division and proliferation (gene therapy).

What is claimed is:

1. A transgenic *Drosophila melanogaster* strain whose genome comprises (i) a first transgene, comprising a cDNA encoding a human β-Bradeion protein operably linked to a promoter comprising a UAS, and (ii) a second transgene, comprising a cDNA encoding a GAL4 protein operably linked to a Glass promoter, wherein a GAL4 binding site in the promoter is bound by the Gal4 protein, expressed specifically in compound eyes, and wherein
   (a) said Bradeion protein is expressed in the compound eyes during development thereof; and
   (b) the compound eyes show rough eye, in which the cell cycles of each single eye are inconsistent due to the expression of said Bradeion protein.

* * * * *